(12) United States Patent
Bokade et al.

(10) Patent No.: US 8,722,935 B2
(45) Date of Patent: May 13, 2014

(54) PROCESS FOR CONVERSION OF ISOBUTYLENE TO TERTIARY BUTYLAMINE

(75) Inventors: Vijav Vasant Bokade, Pune (IN); Praphulla Narahar Joshi, Pune (IN); Prashant Suresh Niphadkar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/704,726

(22) PCT Filed: Jun. 17, 2011

(86) PCT No.: PCT/IN2011/000406
§ 371 (c)(1), (2), (4) Date: Dec. 17, 2012

(87) PCT Pub. No.: WO2011/158258
PCT Pub. Date: Dec. 22, 2011

(65) Prior Publication Data
US 2013/0096349 A1    Apr. 18, 2013

(30) Foreign Application Priority Data
Jun. 18, 2010    (IN) .......................... 1419/DEL/2010

(51) Int. Cl.
*C07C 209/60*    (2006.01)

(52) U.S. Cl.
USPC .......................................................... 564/485

(58) Field of Classification Search
None
See application file for complete search history.

(56) References Cited

U.S. PATENT DOCUMENTS

| 5,107,027 | A | * | 4/1992 | Knifton et al. | 564/485 |
| 5,304,681 | A | * | 4/1994 | Knifton et al. | 564/485 |
| 5,648,546 | A | * | 7/1997 | Bergfeld et al. | 564/485 |

OTHER PUBLICATIONS

Lequitte et al. Journal of Catalysis (1996), 163, p. 255-261.*
Deeba et al., Journal of Organic Chemistry (1988), 53(19), p. 4594-4596.*

* cited by examiner

*Primary Examiner* — Brian J Davis
(74) *Attorney, Agent, or Firm* — Abelman, Frayne & Schwab

(57) ABSTRACT

The invention discloses an improved process for the conversion of isobutylene to tertiary butylamine with conversion up to 50% at pressure lower than 40 bar.

4 Claims, 1 Drawing Sheet

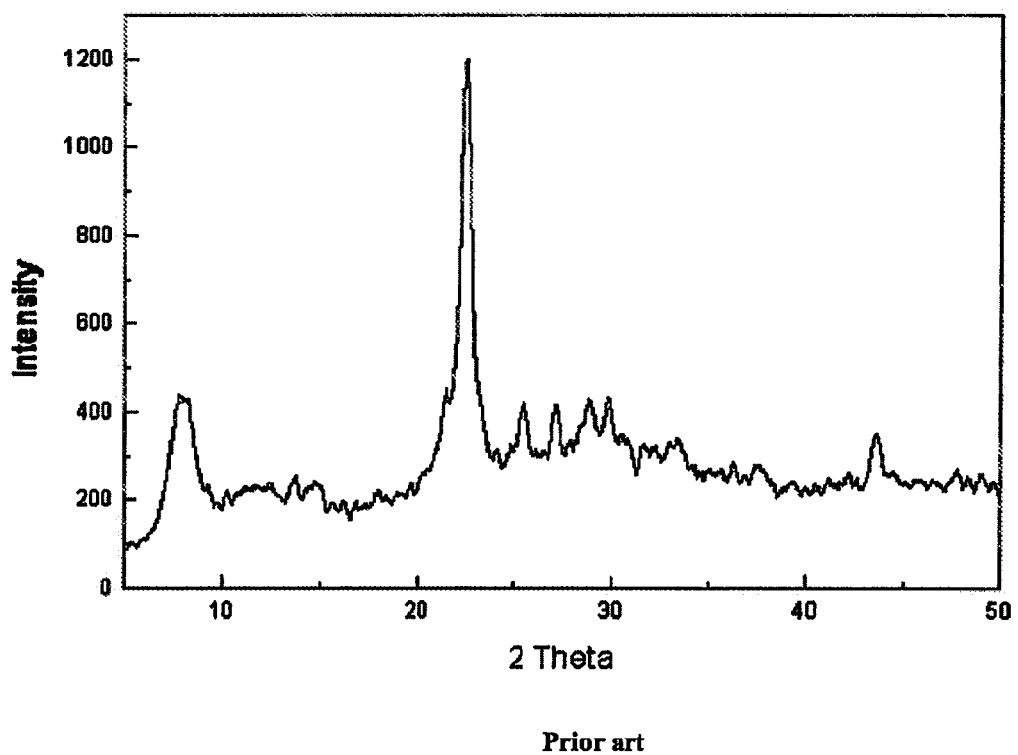
Prior art

PROCESS FOR CONVERSION OF ISOBUTYLENE TO TERTIARY BUTYLAMINE

TECHNICAL FIELD OF INVENTION

This invention discloses an improved process for the conversion of isobutylene to tertiary butylamine up to 50% at low pressure and low temperature with improved yield and conversion.

BACKGROUND AND PRIOR ART

Chemical process scientists and engineers have been continuously studying the subject of manufacture of amines by the amination of olefins. This has also been the subject matter of many patents. Continuous improvements have been made over several years of research, but there is still a tremendous scope to improve yield, conversion rates and in choice of catalyst.

U.S. Pat. Nos. 4,307,250 and 4,375,002 to Peterson et al claims a process for vapor phase catalytic amination for the production of amines wherein an olefin is reacted at a temperature and pressure sufficient to effect formation of the amine, but controlled to prevent polymer formation. The temperature is from 200 degree C.-450 degrees C. and the pressure from 300-6,000 psig using an alumino silicate, e.g. a zeolite catalyst. The selectivity obtained is greater than 95% and the conversion is 3-20%.

EP 0305564 pertains to an improved catalytic process for the amination of C 2-8 olefins, the catalyst being a dealuminized zeolite having an increased Si:Al molar ratio over original zeolite. The dealuminized H-mordenite catalyst is particularly effective for the amination of isobutylene to give tert-butyl amine, at a pressure of 600-1100 psig.

U.S. Pat. No. 6,809,222 (EP1289925) discloses and claims aliphatic amines that are obtained by continuous addition of ammonia to $C_2$ to $C_8$ alkenes (specifically isobutylene) in the presence of a heterogeneous or homogeneous catalyst such as zeolite catalyst like ZSM-5-type at a pressure of 300-1200 psig [2 to 8 MPa] [20-80 bar], a temperature of 220 to 320° C. and a molar ratio of ammonia to the alkene of 1.5 to 20. The conversion of isobutylene to tert-butylamine is 5% and the selectivity is 99.5%. The ratio of silica to alumina is not mentioned.

An article titled "Amination of butanes over protonic zeolites" by M. Lequitte et. al; published in Journal of Catalysis of October 1996, Vol 163, Issue 2, page 255-261 investigated the reaction of 1-butene and isobutene with ammonia. Several zeolites were compared in standard conditions (molar ratio ammonia/olefin=1, total pressure 4 MPa, 600 psig) at different temperatures. The major product of the reaction of isobutene is tert-butylamine, which is formed with high selectivity at low temperature. In the conditions of reaction (4 MPa), the thermodynamic equilibrium at 250° C. is about 20% conversion into tert-butylamine.

CA2092964 relates to method for preparation of alkylamines comprising reacting ammonia or an amine and an olefin containing 2 to 10 carbon atoms per molecule wherein the olefin is isobutylene, in a molar ratio of from 1:1 to 10:1 preferably 2:1, in the presence of a catalyst comprising a zeolite beta having silica-alumina molar ratio of 10:1 to 100:1 at a temperature of 100° C. to 350° C. specifically 260° to 300° C. and a pressure of (68.95-344.74 bar) 1000 psig to 5000 psig preferably 1500 psig to 3500 psig and a liquid hourly space velocity of 0.1 to 10.0 $h^{-1}$.

OBJECTIVE OF THE PRESENT INVENTION

The main objective of the present invention is to provide an improved process for the conversion of isobutylene to tertiary butylamine with improved conversion up to 50% in comparison to prior art processes.

Another objective of the present invention is to provide an improved process for the conversion of isobutylene to tertiary butylamine with at least 90% selectivity of tertiary butylamine.

The objective of the invention is to present a process that is conducted at low temperature and pressure for the conversion of isobutylene to tert-butyl amine.

SUMMARY OF THE INVENTION

Accordingly, the present invention provides an improved process for the conversion of isobutylene to tertiary butylamine up to 50% at low pressure and low temperature with improved yield and conversion.

In an embodiment of the present invention an improved process for the conversion of isobutylene to tertiary butylamine, wherein said process comprises:
  a) contacting isobutylene and ammonia in the presence of a catalyst at a temperature in the range of 200-300° C. with ammonia or ammonia, hydrogen mixture pressure in the range of 20-33 bar, weight hourly space velocity (WHSV, $h^{-1}$) in the range of 3-5, ammonia to isobutylene molar ratio in the range of 3-5 for a period of 15-100 hrs,
  b) cooling the reaction mixture of step (a) to a temperature in the range of 10-30° C. and
  c) separating the unreacted isobutylene, ammonia and byproducts from reaction mix as obtained in step (b) to obtain tert-butyl amine by distillation.

In another embodiment of the present invention a catalyst used in step (a) is solid zeolite of BEA structure with Si:Al ratio in the range of 12.5:1 to 125:1.

In another embodiment of the present invention the selectivity of tertiary butylamine is in the range of 93-95%.

In another embodiment of the present invention the yield of tertiary butylamine is in the range of 12-45%.

In another embodiment of the present invention ammonia in step (a) is used alone or mixture with hydrogen thereof.

In another embodiment of the present invention, the present invention provides an improved process for the conversion of isobutylene to tertiary butylamine in the range of 12-50%.

BRIEF DESCRIPTION OF DRAWING

FIG. 1: X-ray diffraction pattern for BEA Zeolite.

DETAILED DESCRIPTION OF INVENTION

The conversion of isobutylene to tert-butyl amine is carried out by a process catalyzed by a solid zeolite, with BEA structure, resulting in a conversion of 12-50%. The BEA structured zeolite catalyst of the invention has silica:alumina ratio of 12.5:1. The process of the invention comprises:
  a. contacting isobutylene and ammonia in the presence of solid zeolite of BEA structure as catalyst, at a temperature in the range of 200-300° C., ammonia and/or hydrogen ((it could be ammonia alone or ammonia and hydrogen pressure mixture thereof) pressure in the range of 20-33 bar, weight hourly space velocity (WHSV, H$^{-1}$) in the range of 3-5, ammonia to isobutylene molar ratio in the range of 3-5, for a period of 15-100 hrs, b. cooling the reaction mixture of step (a) to a temperature in the range of 10-30° C. and c. separating the unreacted isobutylene, ammonia and by-product by distillation to obtain tert-butyl amine or isolating tert-butyl amine from unreacted isobutylene, ammonia and by-products from reaction mix of step (b) by distillation.

The conversion by the process of the invention is 12-50% with selectivity to tert-butyl amine being 93 to 100% as exemplified herein.

The process of preparation of tertiary butyl amine of the invention is compared by using ZSM-5 catalyst, (Zeolite of pore size 5 microns from M/S Mobil) in examples 1-6. The conversion to tertiary butyl amine by the process of invention and selectivity towards to tertiary butyl amine is higher using zeolite BEA catalyst in comparison to ZSM-5 catalyst as exemplified herein.

EXAMPLES

The following examples are given to illustrate the process of the present invention and should not be construed to limit the scope of the present invention.

General Procedure for the Synthesis of Catalyst

The solid zeolite, with BEA structure is prepared by as-synthesized hydrothermal route without any post dealumination step for the removal of excess alumina to get required Si/Al ratio. The solid zeolite, with BEA structure was prepared by crystallization under hydrothermal condition from the aluminosilicate gel having an oxide molar composition 6.0 (TEA)$_2$O:2.4 Na$_2$O:25.0 SiO$_2$:Al$_2$O$_3$:840.0 H$_2$O. The reagents used were sodium aluminate (43.8% Al$_2$O$_3$, 39.0% Na$_2$O), Silica sol (40% SiO$_2$), tetraethyl ammonium hydroxide (TEAOH, aq. 30% wt/wt solution), sodium hydroxide (AR) and deionized water. The final homogeneous reaction mixture was added into stainless steel autoclave, which after being sealed was placed in an air heated oven maintained at 140° C. for 72 h. After 72 h, the autoclave was taken out of the oven and quenched to room temperature. The solid product was separated by centrifugation/filtration, washed thoroughly with deionized water and then dried at 120° C. in a static air oven for 12 h. This dried sample was further calcined at 560° C. for 16 h under flowing air. The temperature was increased from room temperature to 560° C. with rate of 2° C./min. The calcined sample thus obtained was further subjected for repetitive ion exchange using 1M ammonium chloride solution (in the proportion 15 ml per gram of solid) for 3 times at 80° C. for 6 h. Excess salt was washed by deionized water until there were no detectable chloride ions and the solid was dried at 100° C. This sample was further subjected to calcination at 500° C. for 6 h under flowing air for converting it into protonic form. The final powder sample was then formulated into extrudates in a zeolite:alumina binder ratio of 60:40.

BET Surface area: 600 m$^2$/gm
Particle size by SEM: 0.15 μm
(SiO$_2$/Al2O3)$_{molar}$: 25

General Procedure for the Synthesis of Tert-Butyl Amine

The process of the invention comprises:

a. contacting isobutylene and ammonia in the presence of solid zeolite of BEA structure as catalyst, at a temperature in the range of 200-300° C., ammonia and/or hydrogen pressure (it could be ammonia alone or ammonia and hydrogen pressure mixture thereof) in the range of 20-33 bar, weight hourly space velocity (WHSV, h$^{-1}$) in the range of 3-5, ammonia to isobutylene molar ratio in the range of 3-5, for a period of 15-100 hrs, b. cooling the reaction mixture of step (a) to a temperature in the range of 10-30° C. and c. separating the unreacted isobutylene, ammonia and by-product by distillation to obtain tert-butyl amine or isolating tert-butyl amine from unreacted isobutylene, ammonia and by-products from reaction mix of step (b) by distillation.

The ammonia/isobutylene molar ratio in the process of the invention varies between 3-5 and the WHSV h$^{-1}$ varies between 3-5.

Example 1

Temperature 250° C., pressure 30 bar, Si/Al ratio of 125 (ZSM-5) at NH$_3$/Isobutylene molar ratio of 3.97 and WHSV of 3.98, Time on stream-30 h resulted in a conversion of 12.8% with 100% selectivity towards tert-butyl amine and tert-butyl amine yield of 12.8%.

Example 2

Temperature 250° C., pressure 30 bar, Si/Al ratio of 125 (ZSM-5) at NH$_3$/Isobutylene molar ratio of 4.14 and WHSV of 3.69, Time on stream-30 h resulted in a conversion of 22.53% with 97% selectivity towards tert-butyl amine and tert-butyl amine yield of 21.85%.

Example 3

Temperature 250° C., pressure 30 bar, Si/Al ratio of 125 (ZSM-5) at NH$_3$/Isobutylene molar ratio of 4.02 and WHSV of 4.08, Time on stream-30 h resulted in a conversion of 17.9% with 96.3% selectivity towards tert-butyl amine and tert-butyl amine yield of 17.23%.

Example 4

Temperature 250° C., pressure 30 bar, Si/Al ratio of 20 (ZSM-5) at NH$_3$/Isobutylene molar ratio of 4.27 and WHSV of 3.95, Time on stream-30 h resulted in a conversion of 31.52% with 98.7% selectivity towards tert-butyl amine and tert-butyl amine yield of 31.11%.

Example 5

Temperature 250° C., pressure 30 bar, Si/Al ratio of 20 (ZSM-5) at NH$_3$/Isobutylene molar ratio of 3.96 and WHSV of 4.68, Time on stream-30 h resulted in a conversion of 31.4% with 98.7% selectivity towards tert-butyl amine and tert-butyl amine yield of 30.99%.

Example 6

Temperature 250° C., pressure 33 bar, Si/Al ratio of 20 (ZSM-5) at NH$_3$/Isobutylene molar ratio of 4.01 and WHSV of 4.46, Time on stream-30 h resulted in a conversion of 31.4% with 98% selectivity towards tert-butyl amine and tert-butyl amine yield of 30.77%.

Example 7

Temperature 250° C., pressure 30 bar, Si/Al ratio of 12.5 (Zeolite BEA) at NH$_3$/Isobutylene molar ratio of 4.11 and WHSV of 3.87, Time on stream-30 h resulted in a conversion of 47.8% with 93.7% selectivity towards tert-butyl amine and tert-butyl amine yield of 44.78%.

Example 8

Temperature 250° C., pressure 27 bar, Si/Al ratio of 12.5 (Zeolite BEA) at $NH_3$/Isobutylene molar ratio of 3.63 and WHSV of 4.44, Time on stream-30 h resulted in a conversion of 42.6% with 95.4% selectivity towards tert-butyl amine and tert-butyl amine yield of 40.64%.

Example 9

Temperature 250° C., pressure 27 bar, Si/Al ratio of 12.5 (Zeolite BEA) at $NH_3$/Isobutylene molar ratio of 3.79 and WHSV of 3.93, Time on stream-30 h resulted in a conversion of 41% with 95.3% selectivity towards tert-butyl amine and tert-butyl amine yield of 39.07%.

Advantages of the Present Invention

1. The process is carried out at low temperature and pressure.
2. At low temperature and pressure conditions, improved conversion is obtained.
3. At low temperature and pressure conditions, improved selectivity is observed.

We claim:

1. An improved process for the conversion of isobutylene to tertiary butylamine, wherein said process comprises:
   a) contacting isobutylene and ammonia in the presence of a Zeolite BEA catalyst which has an Si:Al ratio in the range of 12.5:1 to 125:1 at a temperature in the range of 200-300° C. with ammonia or an ammonia, hydrogen mixture at a pressure in the range of 20-33 bar, a weight hourly space velocity (WHSV, $h^{-1}$) in the range of 3-5, and an ammonia to isobutylene molar ratio in the range of 3-5 for a period ranging between 15-100 hrs,
   b) cooling the reaction mixture of step (a) to a temperature in the range of 10-30° C. and
   c) separating the unreacted isobutylene, ammonia and by-products from the reaction mixture as obtained in step (b) by distillation to obtain tertiary butylamine.

2. The process as claimed in claim 1, wherein the selectivity of tertiary butylamine ranges from 93 to 100%.

3. The process as claimed in claim 1, wherein the yield of tertiary butylamine is in the range of 12-45%.

4. The process as claimed in claim 1, wherein conversion of isobutylene is in the range of 12-50%.

* * * * *